United States Patent
Riesinger

(10) Patent No.: US 10,117,607 B2
(45) Date of Patent: Nov. 6, 2018

(54) HAND-HELD MEASURING DEVICE

(71) Applicant: NAWA HEILMITTEL GMBH, Nürnberg (DE)

(72) Inventor: Thomas Riesinger, Nürnberg (DE)

(73) Assignee: NAWA HEILMITTEL GMBH, Nürnberg (DE)

( * ) Notice: Subject to any disclaimer, the term of this patent is extended or adjusted under 35 U.S.C. 154(b) by 538 days.

(21) Appl. No.: 14/763,265

(22) PCT Filed: Jan. 24, 2014

(86) PCT No.: PCT/DE2014/100019
§ 371 (c)(1),
(2) Date: Aug. 11, 2015

(87) PCT Pub. No.: WO2014/114290
PCT Pub. Date: Jul. 31, 2014

(65) Prior Publication Data
US 2015/0359470 A1    Dec. 17, 2015

(30) Foreign Application Priority Data
Jan. 25, 2013   (DE) .................... 20 2013 100 349 U

(51) Int. Cl.
*A61B 5/00*    (2006.01)
*A61B 5/1455*    (2006.01)
(Continued)

(52) U.S. Cl.
CPC ........ *A61B 5/14539* (2013.01); *A61B 5/0004* (2013.01); *A61B 5/1455* (2013.01);
(Continued)

(58) Field of Classification Search
CPC ... A61B 5/145; A61B 5/1455; A61B 5/14507; A61B 5/14539; A61B 5/14546; A61B 5/6846; A61B 5/6847; A61B 2562/0233
See application file for complete search history.

(56) References Cited

U.S. PATENT DOCUMENTS 6,847,490 B1    1/2005   Nordstrom et al.
2001/0034479 A1   10/2001   Ring et al.
(Continued)

FOREIGN PATENT DOCUMENTS

CA        2307420 A1      3/2001
DE    102010053814 A1      6/2012

OTHER PUBLICATIONS

Translation of International Search Report dated Jun. 27, 2014 for International Application No. PCT/DE2014/100019.

*Primary Examiner* — Eric Winakur
(74) *Attorney, Agent, or Firm* — Erickson Kernell IP, LLC; Kent R. Erickson

(57) ABSTRACT

Described is a hand-held measuring device 1 for measuring the pH value of wounds at a measuring point, wherein the hand-held measuring device 1 comprises a housing 2, a removable protective case 5 which at least partially encloses the housing 2, and a detection and evaluation unit constructed of at least two elements 6, 7, 9. The evaluation unit is designed to process the measured signals detected by the detection unit. At least one element 7 of the detection and evaluation unit is arranged in or on the housing 2 and at least one element 6, 9 of the detection and evaluation unit is designed as a component of the protective case 5.

8 Claims, 3 Drawing Sheets

(51) Int. Cl.
    *A61B 5/145*     (2006.01)
    *G01N 21/80*     (2006.01)
    *A61B 50/30*     (2016.01)
    *A61B 50/00*     (2016.01)

(52) U.S. Cl.
    CPC .............. *A61B 5/445* (2013.01); *A61B 50/30* (2016.02); *G01N 21/80* (2013.01); *A61B 2050/006* (2016.02); *A61B 2560/045* (2013.01); *A61B 2560/0418* (2013.01); *A61B 2560/0431* (2013.01); *A61B 2562/16* (2013.01); *A61B 2562/247* (2013.01); *G01N 2201/0221* (2013.01)

(56) References Cited

U.S. PATENT DOCUMENTS

2002/0061495 A1    5/2002    Mault
2006/0161048 A1    7/2006    Squicciarini

HAND-HELD MEASURING DEVICE

TECHNICAL DOMAIN

The present invention relates to a hand-held measuring device for measuring the pH values of wounds at a measuring point.

PRIOR ART

A medical hand-held measuring device for measuring the pH value and the temperature of wounds is known from DE 20 2010 011 934 U1. The hand-held measuring device comprises a housing with a display for showing the particular measured value, as well as operating elements. A probe with a probe arrangement is provided at one end of the housing. The probe arrangement generates electrical measuring signals corresponding to the pH value to be measured and the temperature to be measured. The probe comprises a coupling section on the probe side and is mechanically as well as electrically connected to the housing at a coupling section on the housing side.

Although the hand-held measuring device from the prior art provides accurate and reproducible measurements, it is limited in terms of its usage times.

SUMMARY OF THE INVENTION

This is where the invention begins. The object of the invention, as characterized in the claims, is to provide a hand-held measuring device that can be used for taking measurements more frequently than the hand-held measuring devices known from the prior art.

In accordance with the invention this object is solved by the hand-held measuring device according to claim 1. Further advantageous details, aspects and embodiments of the present invention are set out in the dependent claims, the description and the example.

The present invention provides a hand-held measuring device for measuring the pH values of wounds at a measuring point. The hand-held measuring device comprises a housing, a removable protective case which at least partially encloses the housing, and a detection and evaluation unit constructed of at least two elements. The evaluation unit is designed to process the measuring signals detected by the detection unit. At least one element of the detection and evaluation unit is arranged in or on the housing and at least one element of the detection and evaluation unit is designed as a component of the protective case.

Contamination of the housing by contact with the wound is prevented by the protective case that separates the housing from the measuring point. After measuring the protective case can be removed and replaced by another protective case. In this way the operating times of the hand-held measuring device can be considerably increased. The used protective cases can easily be cleaned and subsequently reused. As at least one element of the detection and evaluation unit is designed as a component of the protective case, measurements falsified through the influence of the protective case are ruled out.

In accordance with a preferred embodiment of the present invention the protective case is designed as a product for single use. As a disposable, the protective case can be changed easily and quickly and after fitting with a new protective case the hand-held measuring device is immediately ready for measuring again. Subsequent cleaning of the protective case is not required.

Particularly preferably the protective case encloses the housing completely and in manner that is sealed off from the surroundings. In this embodiment contamination of the housing is reliably prevented.

Preferably the housing of the hand-held measuring device comprises a first housing section and a rod-like or probe-like second housing section adjoining the first housing section, wherein the second housing section has a reduced cross section as compared to the first housing section. This embodiment of the hand-held measuring device has proven to be particularly advantageous when carrying out measurements.

Particularly preferably the protective case is least constructed in two parts, of a first protective case section enclosing the first housing section and a second protective case section enclosing the second housing section. The at least one element of the detection and evaluation device designed as a component of the protective case is thus designed as a component of the second protective case section.

In accordance with a further preferred embodiment, the at least one element of the detection and evaluation unit designed as a component of the protective case is an optical sensor element, the optical properties of which, such as, for example, absorbing capacity, transparency or reflectivity, change in dependence on the pH value at the measuring point. At the same time an opto-electronic unit is envisaged on the housing as an element of the detection and evaluation unit. After measuring the optical sensor element is disposed of with the protective case. For each new measurement a new sensor element is thus available that guarantees precise and reproducible pH value measurement.

Materials with optical properties that change in dependence on the pH value are well-known to a person skilled in the art. In addition to pH-dependent changes in absorption capacity, transparency or reflectivity, fluorescing substances can also be used. The operating mode of such sensor elements, which are mostly designed in the form of films, is based on the migration of protons into a matrix arranged on a transparent carrier film containing bound fluorophores, the fluorescent properties of which change in accordance with the pH value.

In addition, an embodiment is also particularly preferred in which the at least one element of the detection and evaluation unit designed as a component part of the protective case is an electrical detection element. In this case, an evaluation unit for processing the measuring signals detected by the detection unit is provided in or on the housing as an element of the detection and evaluation unit. After measuring the electrical detection element is disposed of with the protective case. For each new measurement a new detection element is thus available that guarantees precise and reproducible pH value measurement.

Particularly preferably the evaluation unit arranged in or on the housing has a contact field with at least one electrical contact for contacting the electrical detection element. In this case, the transmission of the measuring signals corresponding to the measured pH values from the detection unit to the evaluation unit accommodated in the housing takes place in that during the measurement at least one contact of a contact field provided on the housing produces an ohmic connection to the detection element or to at least one measuring contact of the particular detection element.

Preferably, the protective case comprises a circuit and the evaluation unit arranged in or on the housing comprises a first receiver and/or emitter unit interacting with the circuit. The electrical detection element is designed as a component of the circuit, wherein the circuit is designed for the wireless transmission of the measured values detected by the electrical detection element to the receiver and/or sensor unit. In this case, the transmission of the measuring signals corresponding to the measured pH values from the sensor element to the measuring electronics accommodated in the housing takes place via a wireless transmission path. The circuit ensures wireless transmission of the recorded measured values from the detection element to the receiver unit.

Particularly preferred are embodiments according to which the circuit is designed in the form of a RFID and the circuit comprises at least one antenna structure as well as a microprocessor interacting with the electrical detection element. Power is supplied to the microprocessor via a radio signal received by the antenna structure.

In accordance with a further preferred embodiment of the present invention a second emitter and receiver unit is provided in or on the housing, wherein the second emitter and receiver unit interacts with an external computer via a data radio-transmission path.

The protective case preferably comprises a thin transparent material, particularly preferably a suitable plastic material, which allows cost-effective production of this case.

All the described forms of embodiment can be realized on their own or in any combination together with the hand-held measuring device in accordance with the invention.

BRIEF DESCRIPTION OF THE DRAWINGS

The invention shall be described below in more detail by way of examples of embodiment in conjunction with the drawings. It is expressly pointed out here that the invention should not be limited to the given examples. In the drawings

WAYS OF IMPLEMENTING THE INVENTION

Figure 1:
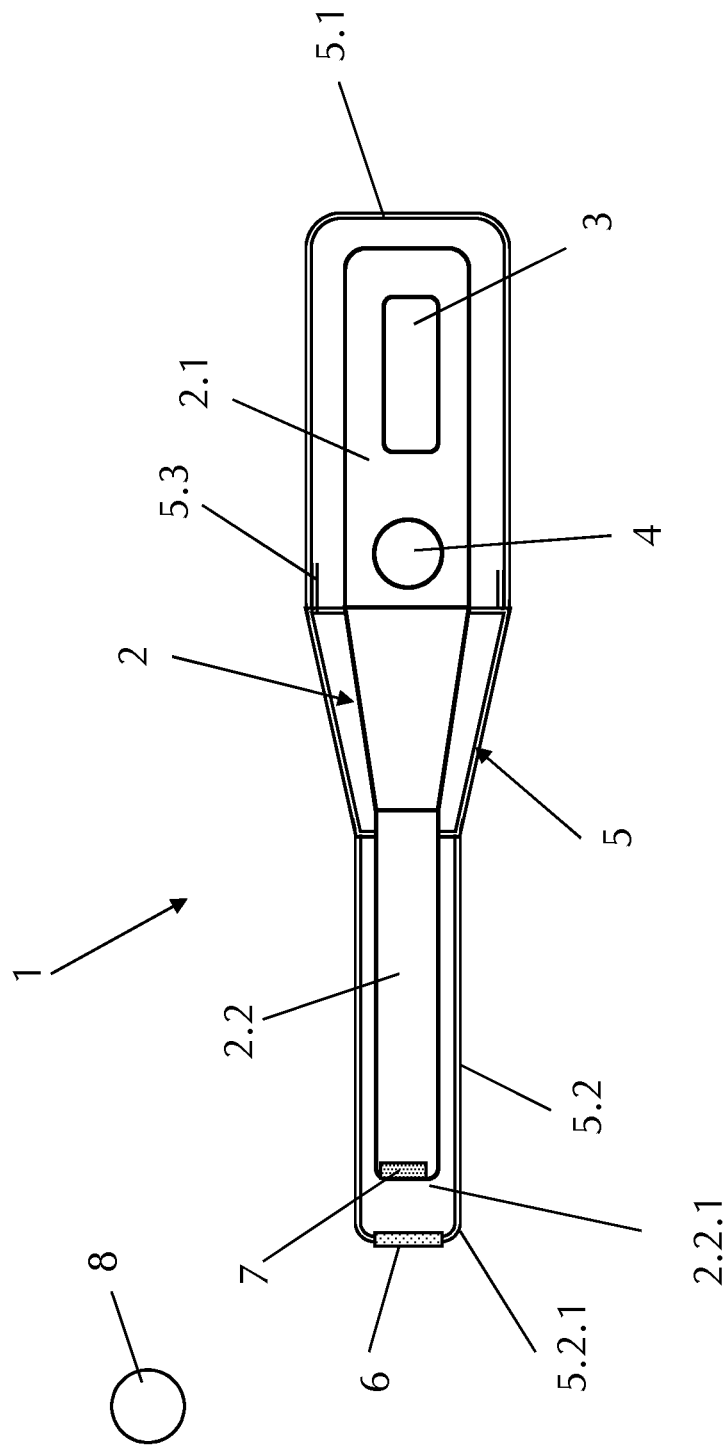
FIG. 1 shows a schematic view from above of a hand-held measuring device in accordance with the invention.

In the FIG. 1 denotes a hand-held measuring device in the form of an electronic pH-meter for measuring the pH value of wounds. In its external design, the housing 2 of the hand-held measuring device 1 comprises a housing section 2.1 with a larger cross section and, adjoining this housing section at the front end, a rod-like or probe-like housing section 2.2 with a reduced cross section. Arranged on the free end of the housing section 2.2 located remotely from the housing section 2.1 an element of a detection and evaluation unit necessary for measurement is provided as is explained below for various possible forms of embodiment of the hand-held measuring device 1 in connection with FIGS. 1 to 3.

Among other things, the housing section 2.1 serves to accommodate, for example, an evaluation unit having a microprocessor, as well as to accommodate a rechargeable battery and a charging current circuit, which, for example, allows contactless charging of this battery, e.g. in an inductive and/or capacitive manner. Further provided on the housing section 2.1 is a display 3 which, among other things, serves to show the operating status of the hand-held measuring device 1 as well as the particular measured value (pH value). Also provided on the housing section 2.1 are operating elements 4, for activating and deactivating the hand-held measuring device, for example. The housing 2 is tightly sealed so that penetration of dirt and/or germs into the interior of the housing 2 is ruled out.

In the figures, 5 denotes a protective case which is made of a thin, flexible and transparent material, for example a suitable plastic material in the form of a film. During use of the hand-held measuring device 1, the housing 2 is enclosed in the protective case 5 to protect it against exposure to dirt and/or germs.

In the embodiment shown in the figures, the protective case 5, which when enclosing the housing 2 is adapted to the shape of the housing 2, is designed in two parts, namely consisting of a protective case section 5.1 essentially accommodating the housing section 2.1, and a protective case section 5.2 which, adapted to the reduced cross-section of the housing section 2.2 also has a reduced cross section as compared to the protective case section 5.1. When the protective casing 5 is fastened to the housing 2, both protective case sections 5.1 and 5.2 are connected to each other in the connection area 5.3 in a sealed, but detachable manner. In the embodiment shown this connection area is arranged approximately in the middle of the housing 2 between the ends of the housing sections 2.1 and 2.2 facing away from each other.

The protective case 5 is designed as an article for single use, i.e. after each use of the hand-held measuring device 1 the protective case 5 is removed from the housing 2 and disposed of. On the one hand, contamination of the housing 2 with dirt and/or germs is prevented by the protective case 5 when the hand-held measuring device 1 is being used. On the other hand, the sterile protective case 5 newly applied to the housing before every use of the hand-held measuring device 1 also ensures that no germs are transmitted from the housing 2 to the measuring area (e.g. wound).

Measurement of the pH value takes place through the closed protective case 5 or through the closed protective case section 5.2. This can be done in different ways.

FIG. 1 shows a schematic view of an embodiment in which the measurement of the pH value by the hand-held measuring device 1 takes place optically, i.e. by way of an optical sensor element. For this, on its front end 5.2.1, which is adjacent to the free end 2.2.1 of housing section 2.2, the protective case section 5.2 is provided with a window 6 acting as an optical sensor element having optical transmittance characteristics in terms of absorption, reflectivity and/or transparency which change in dependence on the pH value prevailing at the measuring site. An opto-electronic unit 7 with an opto-electronic sensor is provided at the free end 2.2.1 of the housing section 2.2. After measuring and/or during measuring, the light from a light source 8 is directed through the window 6 onto the opti-electronic unit 7 which then supplies an electrical measuring signal corresponding to the current transmittance characteristics and thereby the measured pH value to the measuring electronics in the housing 2. The light source 8 can also be arranged on or in the housing 2 or in the opto-electronic unit 7, wherein in this case the light reflected by the sensor element 6 in the direction of the opto-electronic unit 7 is detected.

Figure 2:
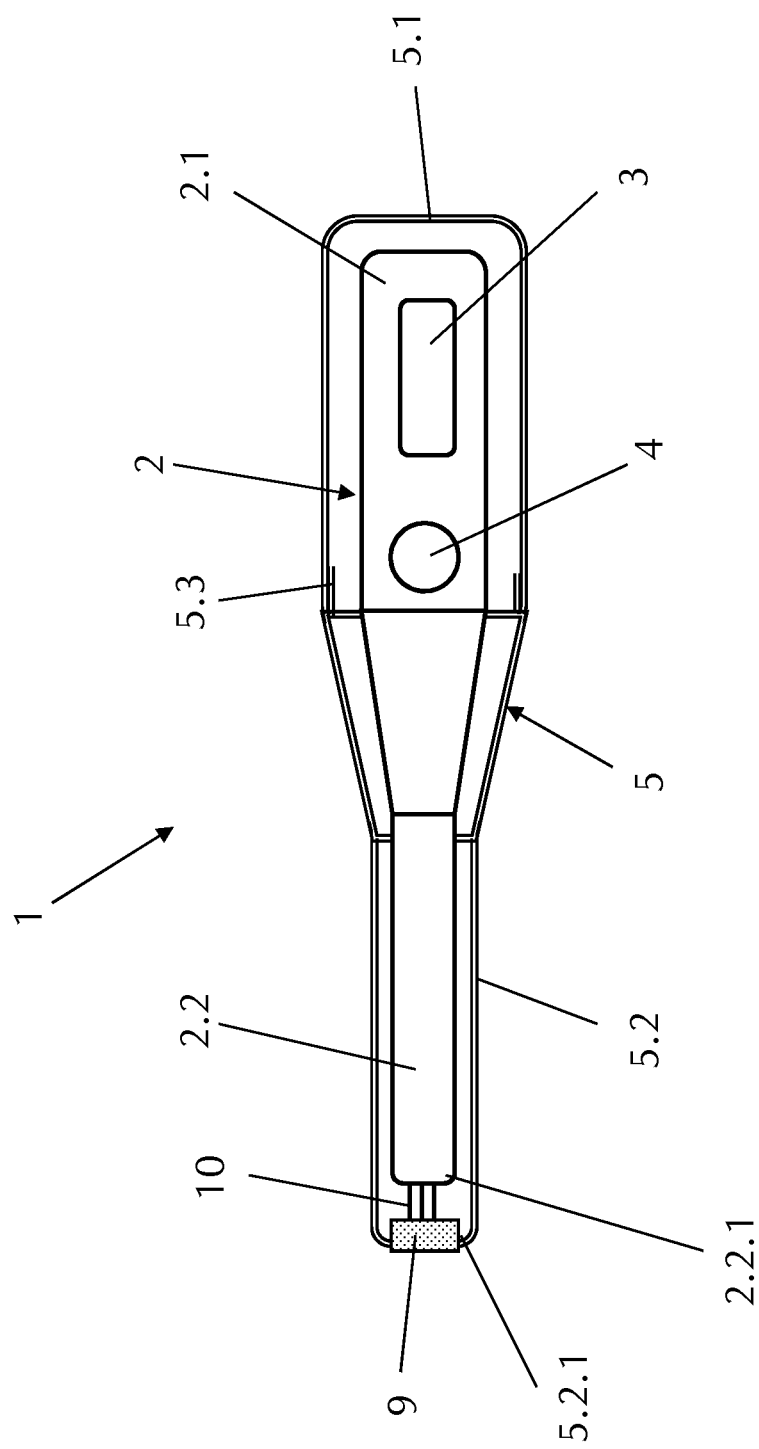
FIG. 2 shows a schematic view from above of a further embodiment of the hand-held measuring device in accordance with the invention.

FIG. 2 shows an embodiment in which on the front end 5.2.1 of the protective case section 5.1 a sensor element 9 (for example an ISFET sensor) is provided, which delivers an electrical measuring signal that is dependent on the measured pH value. Here, the sensor element 9 has its sensor area outside the protective case section 5.2 and its electrical connections or electrodes inside this protective case section, wherein the interior of the protective case section 5.2 is also hermetically sealed off from the surroundings in the region of the sensor element 9. In this form of embodiment, the housing section 2.2 is provided at its end 2.1.1 with electrical contacts 10, in the form of contact pins, for example, which when in use produce an electrical connection with the 5 contacts of the sensor element 9.

Figure 3:
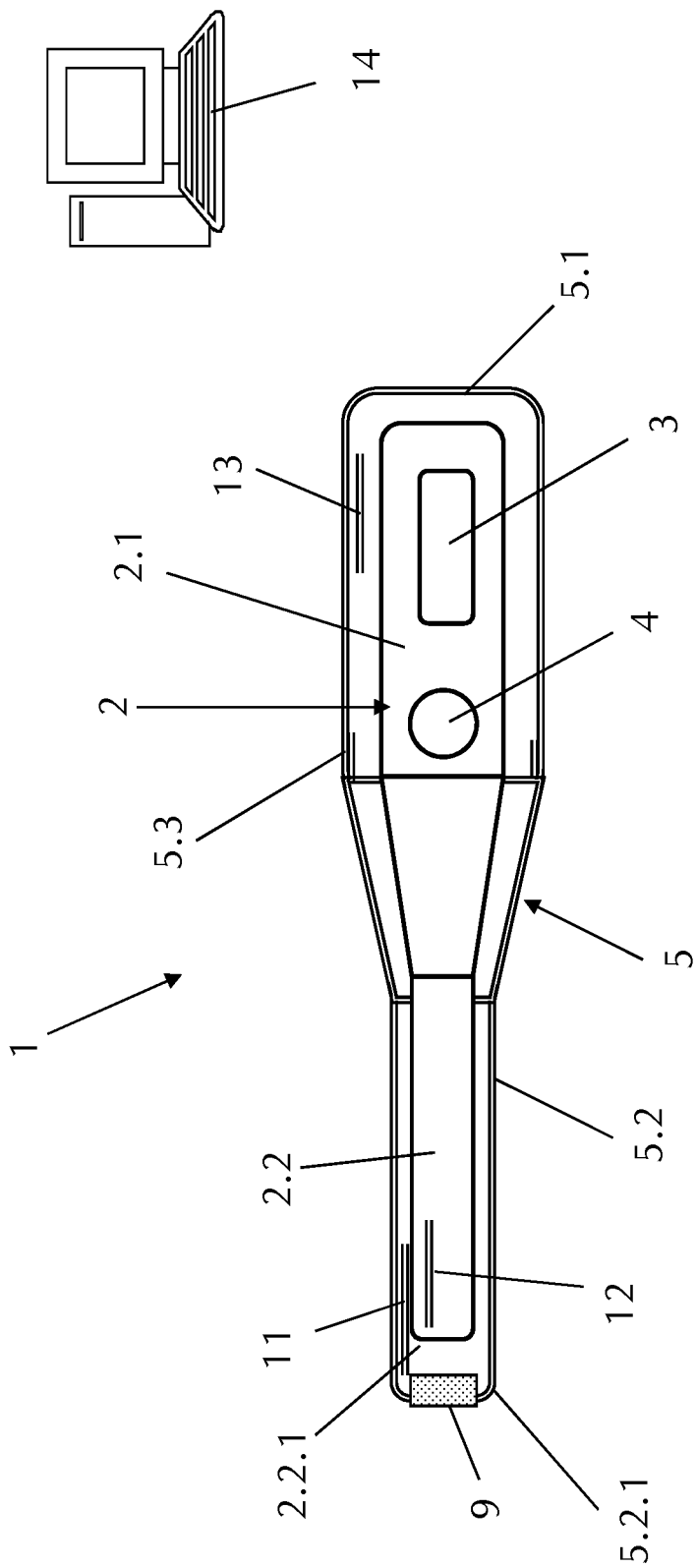
FIG. 3 shows a schematic view from above of a further embodiment of the hand-held measuring device in accordance with the invention.

As a further possibility, FIG. 3 shows an embodiment in which the protective case section 5.2 at its front end again comprises the sensor element 9, but which is a component part of an electrical circuit 11, designed as an RFID or RFID-TAG with a microprocessor in such a way that the measuring data corresponding to the pH values delivered by the sensor element 9 are transmitted wirelessly, i.e. via electromagnetic waves, to a receiver and emitter unit 12 arranged in the interior of the housing section 2.2. For this, the circuit 11 is set up, for example, as is known for RFIDs and comprises, among other things, an antenna structure, the microprocessor as well as a power supply for the microprocessor which is supplied from the radio signals of the receiver and emitter unit 12. In contrast to conventional, simple RFIDs, the circuit 11 is designed so that its radio frequency signal is modulated in accordance with the measured pH value.

LIST OF REFERENCE NUMBERS

1 Hand-held measuring device
2 Housing
2.1, 2.2 Housing section
2.2.1 Front end of the housing section 2.2
3 Display
4 Operating element
5 Protective case
5.1, 5.2 Protective case section
5.2.1 Front end of the protective case section
6 Optical sensor element or window
8 Light source
9 Electrical detection element
10 Contact
11 Circuit
12 Receiver and emitter unit
13 Receiver and emitter unit
14 Computer

The invention claimed is:

1. A hand-held measuring device for measuring the pH value of wounds at a measuring point, wherein the hand-held measuring device comprises:
   a housing,
   a removable protective case which at least partially encloses the housing, the protective case comprising a circuit; and
   a detection and evaluation unit constructed of at least two elements, comprising an evaluation unit designed to process measuring signals detected by a detection unit, wherein
      at least one element of the detection and evaluation unit comprising the detection unit arranged in or on the housing; and
      at least one element of the detection and evaluation unit is an electrical detection element which is designed as a component of the protective case;
      wherein the evaluation unit is arranged in or on the housing and comprises a first receiver and/or emitter unit interacting with the circuit, and wherein the electrical detection element is a component of the circuit and the circuit is designed for wireless transmission of a measuring value detected by the electrical detection element to the first receiver and/or emitter unit.

2. The hand-held measuring device according to claim 1, wherein the protective case closes the housing completely and in manner that is sealed off from the surroundings.

3. The hand-held measuring device according to claim 1, wherein the housing consists of a first housing section and a rod-like or probe-like second housing section adjoining the first housing section, wherein the second housing section has a reduced cross section as compared to the first housing section.

4. The hand-held measuring device according to claim 3, wherein the protective case is at least constructed in two parts, of a first protective case section enclosing the first housing section and a second protective case section enclosing the second housing section, wherein the at least one element of the detection and evaluation unit designed as a component of the protective case is designed as a component of the second protective case section.

5. The hand-held measuring device according to claim 1, wherein the at least one element of the detection and evaluation unit designed as a component of the protective case is an optical sensor element, the optical properties of which change in dependence on the pH value at the measuring point, and in that on the housing an opto-electronic unit is provided as an element of the detection and evaluation unit.

6. The hand-held measuring device according to claim 1, wherein an evaluation unit arranged in or on the housing has a contact field with at least one electrical contact for contacting the electrical detection element.

7. The hand-held measuring device according to claim 1, wherein the circuit is designed in the form of a RFID and has at least one antenna structure as well as a microprocessor interacting with the electrical detection element, and in that power is supplied to the microprocessor via a radio-communication signal which can be received by the antenna structure.

8. The hand-held measuring device according to claim 1, wherein on or in the housing a second receiver and emitter unit is provided, wherein the second receiver and emitter unit interacts with an external computer via a data transmission path.

* * * * *